United States Patent [19]

Honda

[11] 4,404,063
[45] Sep. 13, 1983

[54] METHOD FOR THE SEPARATION OF INDOLE

[75] Inventor: Tadatoshi Honda, Hiratsuka, Japan

[73] Assignee: Mitsui Toatsu Chemicals, Inc., Tokyo, Japan

[21] Appl. No.: 423,094

[22] Filed: Sep. 24, 1982

[30] Foreign Application Priority Data

Oct. 8, 1981 [JP] Japan .................. 56-159441

[51] Int. Cl.$^3$ .................. B01D 3/34; C07D 209/04
[52] U.S. Cl. .......................... 203/6; 203/29; 203/33; 203/36; 203/37; 203/38; 548/469; 548/508
[58] Field of Search .......... 548/469, 508; 203/33, 203/6-9, 29, 36, 37, 38, 39, 40

[56] References Cited

U.S. PATENT DOCUMENTS

| | | | |
|---|---|---|---|
| 2,409,676 | 10/1946 | Gresham et al. | 548/508 |
| 2,412,651 | 12/1946 | Riethof | 203/37 |
| 2,708,653 | 5/1955 | Sisco et al. | 203/37 |
| 2,916,496 | 12/1959 | Anderson | 548/469 |
| 2,916,497 | 12/1959 | Murray et al. | 548/469 |
| 3,255,205 | 6/1966 | Robinson | 548/508 |
| 3,886,178 | 5/1975 | Petinaux et al. | 548/508 |

*Primary Examiner*—Bascomb, Jr. Wilbur L.
*Attorney, Agent, or Firm*—Fisher, Christen & Sabol

[57] ABSTRACT

A method for the separation of indole by distilling an indole-containing reaction fluid obtained by the reaction of aniline with ethylene glycol or by the reaction of N-($\beta$-hydroxyethyl)aniline, which comprises bringing the reaction fluid into contact with a basic substance prior to and/or during the distillation. This method can prevent the deterioration of indole during the distillation procedure.

10 Claims, No Drawings

METHOD FOR THE SEPARATION OF INDOLE

BACKGROUND OF THE INVENTION

1. Field of the Invention

This invention relates to an improved method for the separation of indole by distilling an indole-containing reaction fluid obtained by using N-($\beta$-hydroxyethyl)aniline as the starting material or by using aniline and ethylene glycol as the starting materials.

2. Description of the Prior Art

Indole is known as an important material for use in chemical industry and, especially in recent years, has become essential for the synthesis of perfumes and amino acids.

In the past, many attempts were made to synthesize indole. However, most of the processes so devised had the disadvantages of yielding considerable amounts of by-products, requiring expensive compounds as the starting materials, leading to indole through a lengthy chain of steps and/or involving troublesome operations. Meanwhile, two single-step processes for the preparation of indole from inexpensive compounds have recently been proposed, one using N-($\beta$-hydroxyethyl)aniline as the starting material and the other using aniline and ethylene glycol as the starting materials. The findings of the present inventor have revealed that, in these two processes, the presence of a large amount of aniline in the reaction system is required to obtain indole in good yield. Accordingly, in the preparation of indole by these processes, it is essential to separate and recover the large amount of aniline contained in the resulting reaction fluid. Moreover, the reaction fluid resulting from either of these processes also contains trace amounts of by-products. Thus, the indole obtained by the mere separation of aniline still contains impurities and cannot be directly used as a starting material for the synthesis of perfumes and amino acids.

Even if it is tried to separate indole by distilling such a reaction fluid, a part of the indole contained in the reaction fluid is deteriorated (i.e., converted into a tarry substance) in the course of the distillation to cause a considerable loss of indole. As a result, the amount of indole thus obtained is significantly smaller than that of indole initially present in the reaction fluid.

SUMMARY OF THE INVENTION

It is an object of the present invention to provide a method which permits the separation of indole by distillation without causing any deterioration thereof.

The loss of indole due to its deterioration during the distillation procedure becomes smaller according as the total pressure employed for the distillation is lowered and according as the distillation time is reduced. However, as illustrated by the comparative example given later, it has been demonstrated that a considerable loss of indole occurs even under such mild distillation conditions as are practicable in industrial applications. The present inventor has now found that such deterioration of indole during the distillation procedure can be substantially prevented by bringing the indole-containing reaction fluid into contact with a basic substance prior to and/or during the distillation.

According to the present invention, there is provided in a method for the separation of indole by distilling an indole-containing reaction fluid obtained by the reaction of aniline with ethylene glycol or by the reaction of N-($\beta$-hydroxyethyl)aniline, the improvement which comprises bringing the reaction fluid into contact with a basic substance prior to and/or during the distillation, whereby the deterioration of indole during the distillation procedure is substantially prevented.

DETAILED DESCRIPTION OF THE INVENTION

At present, there are a variety of well-known processes for the preparation of indole by using N-($\beta$-hydroxyethyl)aniline as the starting material or by using aniline and ethylene glycol as the starting materials. By way of example, one process using N-($\beta$-hydroxyethyl)aniline as the starting material comprises reacting N-($\beta$-hydroxyethyl)aniline in the vapor phase at a temperature of 200° to 500° C. in the presence of a catalyst such as a copper- or silver-containing catalyst, with an equimolar or greater amount of aniline used as the diluent. Another process using aniline and ethylene glycol as the starting materials comprises reacting 1 mole of ethylene glycol with 2 moles or more of aniline in the vapor phase, a mixed vapor-liquid phase, or the liquid phase at a temperature of 200° to 500° C. in the presence of a catalyst such as a solid acid catalyst or a metal salt.

Various processes for the preparation of indole by using N-($\beta$-hydroxyethyl)aniline as the starting material or by using aniline and ethylene glycol as the starting materials are disclosed in the following references:

Processes using N-($\beta$-hydroxyethyl)aniline as the starting material are disclosed, for example, in Japanese Patent Laid-Open Nos. 105663/'80 and 108850/'80. Processes using aniline and ethylene glycol as the starting materials are disclosed, for example, in Japanese Patent Laid-Open Nos. 36451/'81, 46865/'81, 53652/'81, 55366/'81, 63958/'81, 86154/'81, 110672/'81, 150062/'81, and 169668/'81.

The manner in which the indole-containing reaction fluid is brought into contact with a basic substance may vary according to the type of basic substance used. The contact can be effected, for example, (a) by adding a basic substance directly to the reaction fluid and dissolving or suspending the former in the latter, (b) by adding an aqueous solution of a water-soluble basic substance to the reaction fluid and stirring this mixture at any desired temperature, or (c) by passing the reaction fluid through a column packed with a basic substance. Of course, the present invention is not limited to these procedures and it is possible to employ any other procedure that permits the reaction fluid to come into contact with a basic substance.

The basic substances which can be used in the method of the present invention include oxides, hydroxides, and hydrides of alkali metals or alkaline earth metals, alkali metal carbonates, alkali metal amides, alkali metal alkoxides, quaternary ammonium hydroxides, tertiary amines, ion exchange resins and other ion exchangers, and the like. More specifically, they include alkali metal oxides such as sodium oxide, potassium oxide, lithium oxide, rubidium oxide, and cesium oxide; alkaline earth metal oxides such as beryllium oxide, magnesium oxide, calcium oxide, strontium oxide, and barium oxide; alkali metal hydroxides such as sodium hydroxide, potassium hydroxide, lithium hydroxide, rubidium hydroxide, and cesium hydroxide; alkaline earth metal hydroxides such as beryllium hydroxide, magnesium hydroxide, calcium hydroxide, strontium hydroxide, and barium hydroxide; alkali metal carbonates such as sodium carbonate, potassium carbonate, lithium carbonate, rubidium carbonate, and cesium carbonate; alkali metal hydrides such as sodium hydride, potassium hydride, and lithium hydride; and alkaline earth metal hydrides such as beryllium hydride, magnesium hydride, and calcium hydride. Alkali metal amides are compounds derived from ammonia by replacement of hydrogen by an alkali metal, and specific examples thereof are sodium amide, potassium amide, lithium amide, etc. Alkali metal alkoxides are compounds derived from an alcohol by replacement of the hydroxyl hydrogen by an alkali metal, and specific examples thereof are sodium methoxide, sodium ethoxide, sodium t-butoxide, potassium methoxide, potassium ethoxide, potassium t-butoxide, etc. Specific examples of quaternary ammonium hydroxides are tetramethylammonium hydroxide, tetraethylammonium hydroxide, tetra-n-propylammonium hydroxide, tetra-n-butylammonium hydroxide, triethylbenzylammonium hydroxide, tricaprylammonium hydroxide, trimethyllaurylammonium hydroxide, etc. and specific examples of tertiary amines are trimethylamine, triethylamine, tri-n-propylamine, tri-n-butylamine, tricaprylmethylammonium hydroxide, diethylbenzylamine, dicaprylmethylamine, dimethyllaurylamine, N,N-dimethylaniline, dimethylamino-$\Delta^1$-pyrroline, 1,5-diaza-bicyclo[4,3,0]nonene-5, 1,8-diazabicyclo[5,4,0]undecence-7, etc. In addition, useful ion exchange resins include strongly basic resins in free or hydroxide form, and useful ion exchangers include various substances exhibiting anion exchange phenomena, such as anion exchange cellulose, anion exchange type of Sephadex, anion/exchange liquid, basic dolomite, hydrated iron oxide, hydrated zirconium oxide, etc.

Among the foregoing basic substances, oxides and hydroxides of alkali metals or alkaline earth metals, alkali metal carbonates, quaternary ammonium hydroxides, tertiary amines, ion exchange resins, and other ion exchangers are preferred. The most preferred basic substances are oxides and hydroxides of alkali metals and alkaline earth metals as well as alkali metal carbonates.

Where the contact is effected by adding a basic substance to the indole-containing reaction fluid, the basic substance is usually used in an amount of 0.001 to 0.02 mole per mole of the indole present in the reaction fluid to attain satisfactory results. However, the present invention is not limited to this range of amounts. If desired, the basic substance may be used in any other amount.

According to the method of the present invention, the indole-containing reaction fluid having been treated with the basic substance is then subjected to distillation. Prior to the distillation, the basic substance may be removed from the reaction fluid by liquid-liquid separation of filtration. Alternatively, the reaction fluid containing the basic substance may be directly subjected to distillation. Moreover, the basic substance may be added to the reaction fluid in the course of the distillation.

According to the method of the present invention, the distillation may be carried out under atmospheric or subatmospheric pressure. However, it is preferable to carry it out under subatmospheric pressure because indole is more liable to deteriorate during atmospheric distillation.

The distillation may be carried out in a batchwise or continuous manner.

The method of the present invention is more specifically illustrated by the following examples. However, these examples are not to be construed to limit the scope of the invention.

EXAMPLE 1

Preparation of an Indole-Containing Reaction Fluid

A stainless steel reactor having an internal diameter of 25 mm was packed with 500 ml of a catalyst with particle diameters of 3–4 mm. This catalyst, which had been prepared by coprecipitation, consisted of 30 mole % of CuO, 15 mole % of MgO, 5 mole % of $MnO_2$, and 50 mole % of $SiO_2$ and had a BET surface area of 200 $m^2/g$.

While a gas mixture composed of 0.1 part of hydrogen and 0.9 part of nitrogen was being passed through the reactor at a rate of 10 liters/min, the temperature of the catalyst bed was slowly raised from room temperature to 300° C. Its temperature was kept at 300° C. for 1 hour and then at 330° C. for 1 hour to reduce the catalyst. After completion of the reduction, a gas mixture composed of 0.5 part of hydrogen and 0.5 part of nitrogen was passed through the reactor at a rate of 5 liters/min. Then, N-($\beta$-hydroxyethyl)aniline was reacted by feeding a 15% (w/w) aniline solution thereof to a carburetor at a rate of 700 ml/hr and thereby introducing it into the reactor. During this reaction, the temperature of the catalyst bed was kept at 350° C.

The reaction fluid collected during the period between 4 and 24 hours after the start of the reaction (hereinafter referred to as fluid A) was used for subsequent experiments on the separation of indole by distillation. On analysis, fluid A was found to be an aniline solution containing 9.89% by weight of indole and 0.40% by weight of indoline. When fluid A was extracted with water, the pH of the water used as the extractant was 8.1.

Separation of Indole By Distillation

A distillation flask having a capacity of 1 liter was fitted with a rectifying column having an internal diameter of 50 mm and a height of 350 mm and packed with McMahon packing. Into this distillation flask were charged 500 g of fluid A and 0.7 g of anhydrous potassium carbonate. Then, an experiment on the separation of indole was carried out by distilling fluid A under a reduced pressure of 5 mmHg.

The distillation flask was immersed in an oil bath and its temperature was slowly raised from 60° C. to 100° C. over a period of 3 hours to obtain an aniline fraction. Subsequently, the temperature of the oil bath was slowly raised from 100° C. to 180° C. over a period of 1 hour to obtain an indole fraction.

After completion of the distillation, the inside of the rectifying column was washed with methanol. The methanol washings were combined with the fluid remaining in the distillation flask and the resulting mixture was regarded as a distillation residue. The percent loss of indole during the distillation procedure was calculated by determining the respective indole contents of the aniline fraction, the indole fraction, and the distillation residue and then subtracting the sum of them from the amount of indole initially present in 500 g of fluid A. Thus, no loss of indole during the distillation procedure was recognized.

EXAMPLE 2

Fluid A, which had been prepared in Example 1, was treated with three different basic substances in the following manners:

(a) To a 500-g portion of fluid A was added 0.7 g of tributylamine.

(b) To a 500-g portion of fluid A was added 5 milliequivalents of a strongly basic anion exchange resin in hydroxide form (LEVATIT MP-500; a commercial product of the Bayer Company). This mixture was stirred at room temperature for 30 minutes and then filtered to remove the anion exchange resin.

(c) To a 500-g portion of fluid A was added 50 ml of a 0.1 N aqueous solution of KOH. This mixture was stirred at room temperature for 30 minutes and then subjected to a liquid-liquid separation for removing the aqueous layer.

The separation of indole was carried out by distilling these treated portions of fluid A in the same manner as in Example 1. Thus, no loss of indole during the distillation procedure was recognized.

EXAMPLE 3

Preparation of Indole-Contianing Reaction Fluids

A Pyrex glass reactor having an internal diameter of 15 mm was packed with 50 ml of each of the catalysts (with particle diameters of 1 to 2 mm) listed in Table 1 and then kept at the reaction temperature shown in Table 1. While hydrogen was being passed through the reactor at a rate of 300 ml/min, a 6.3%(w/w) aniline solution of ethylene glycol and water were simultaneously fed to the reactor at rates of 70 ml/hr and 9 ml/hr, respectively. The resulting reaction fluids consisted of an aqueous and an oily layer. The pH of the aqueous layer ranged from 7.5 to 8.3.

Using the oily layers of the reaction fluids collected during the period between 0 and 10 hours after the start of the reaction (hereinafter referred to as fluids B, C, and D as shown in Table 1), the separation of indole by distillation was carried out in the same manner as in Example 1. In all cases, no loss of indole during the distillation procedure was recognized.

TABLE 1

| Fluid | Type of catalyst | Reaction temperature |
|---|---|---|
| B | CdSO$_4$ | 300° C. |
| C | CdS | 300° C. |
| D | MgCl$_2$/activated carbon | 325° C. |

EXAMPLE 4

An indole-containing reaction fluid was prepared in the same manner as in Example 3 (using the CdSO$_4$ catalyst) and each of the basic substances listed in Table 3 was added thereto. Then, the separation of indole by distillation was carried out in the same manner as in Example 1.

TABLE 2

| Basic substance | Amount of basic substance added (g) | Loss of indole (%) |
|---|---|---|
| Magnesium oxide | 0.3 | Unrecognized |
| Calcium hydroxide | 0.6 | " |
| Tetramethylammonium hydroxide | 0.4 | " |
| Lithium amide | 0.1 | " |
| Sodium ethoxide | 0.3 | " |

TABLE 2-continued

| Basic substance | Amount of basic substance added (g) | Loss of indole (%) |
|---|---|---|
| Sodium hydride | 0.02 | " |
| Calcium hydride | 0.3 | 5 |

EXAMPLE 5

A glass tube having an internal diameter of 15 mm and a length of 300 mm was packed with a strongly basic anion exchange resin in hydroxide form (LEVATIT MP-500) to a packing height of 200 mm and then supported vertically. An indole-containing reaction fluid prepared in the same manner as in Example 3 (using the CdS catalyst) was passed therethrough at a rate of 100 ml/min. Using the same apparatus as described in Example 1, the treated reaction fluid was distilled to separate indole therefrom. No loss of indole during the distillation procedure was recognized.

Comparative Example

The separation of indole was carried out by distilling fluids A, B, C, and D in the same manner as in Example 1, except that the addition of anhydrous potassium carbonate was omitted. In all cases, a considerable loss of indole during the distillation procedure was recognized. The percent losses of indole were as shown in Table 4.

TABLE 4

| Fluid | Loss of indole (%) |
|---|---|
| A | 40 |
| B | 38 |
| C | 35 |
| D | 44 |

What is claimed is:

1. In a method for the separation of indole by distilling an indole-containing reaction fluid obtained by the reaction of aniline with ethylene glycol or by the reaction of N-($\beta$-hydroxyethyl)aniline, the improvement which comprises bringing the reaction fluid into contact with a basic substance prior to and/or during the distillation, whereby the deterioration of indole during the distillation procedure is substantially prevented.

2. A method as claimed in claim 1 wherein the basic substance is an alkali metal oxide, an alkaline earth metal oxide, an alkali metal hydroxide, an alkaline earth metal hydroxide, an alkali metal hydride, an alkaline earth metal hydride, an alkali metal carbonate, an alkali metal amide, an alkali metal alkoxide, a quaternary ammonium hydroxide, a tertiary amine, an ion exchange resin, or another ion exchanger.

3. A method as claimed in claim 2 wherein the basic substance is an alkali metal oxide, an alkaline earth metal oxide, an alkali metal hydroxide, an alkaline earth metal hydroxide, an alkali metal carbonate, a quaternary ammonium hydroxide, a tertiary amine, an ion exchange resin, or another ion exchanger.

4. A method as claimed in claim 2 wherein the basic substance is an alkali metal oxide, an alkaline earth metal oxide, an alkali metal hydroxide, an alkaline earth metal hydroxide, or an alkali metal carbonate.

5. A method as claimed in claim 1 wherein the contact is effected by adding the basic substance to the reaction fluid in an amount of 0.001 to 0.02 mole per mole of the indole present in the reaction fluid.

6. A method as claimed in claim 1 wherein the reaction fluid is brought into contact with the basic substance in solid form and then subjected to distillation.

7. A method as claimed in claim 1 wherein the basic substance is added to the reaction fluid, the basic substance is separated from the reaction fluid, and then the reaction fluid is subjected to distillation.

8. A method as claimed in claim 1 wherein the basic substance is added to the reaction fluid and then the reaction fluid is directly subjected to distillation.

9. A method as claimed in claim 6 wherein the basic substance is in solid form and the contact is effected by passing the reaction fluid through a packed bed of the basic substance.

10. A method as claimed in claim 7 or 8 wherein the basic substance is soluble in water and an aqueous solution of the basic substance is added to the reaction fluid.

* * * * *